US006687012B2

(12) United States Patent
Sanzari

(10) Patent No.: US 6,687,012 B2
(45) Date of Patent: Feb. 3, 2004

(54) APPARATUS AND METHOD FOR MEASURING OPTICAL ACTIVITY

(75) Inventor: Martin Sanzari, Elmwood Park, NJ (US)

(73) Assignee: Fordham University, Bronx, NY (US)

(*) Notice: Subject to any disclaimer, the term of this patent is extended or adjusted under 35 U.S.C. 154(b) by 86 days.

(21) Appl. No.: 10/016,476

(22) Filed: Oct. 30, 2001

(65) Prior Publication Data
US 2003/0081221 A1 May 1, 2003

(51) Int. Cl.[7] .................................................. G01B 9/02
(52) U.S. Cl. ........................................ 356/484; 356/491
(58) Field of Search .............................. 356/450, 484, 356/491

(56) References Cited

U.S. PATENT DOCUMENTS

| 4,456,339 A | * | 6/1984 | Sommargren ............... 359/497 |
|---|---|---|---|
| 4,832,492 A | | 5/1989 | Calvani et al. |
| 4,912,059 A | | 3/1990 | Newman et al. |
| 5,036,204 A | | 7/1991 | Leylen |
| 5,398,681 A | | 3/1995 | Kupershmidt |
| 5,448,992 A | | 9/1995 | Kupershmidt |
| 5,619,325 A | | 4/1997 | Yoshida |
| 5,687,721 A | | 11/1997 | Kuhls |
| 5,896,198 A | | 4/1999 | Chou et al. |
| 6,052,186 A | | 4/2000 | Tsai |
| 6,118,536 A | | 9/2000 | Sakamoto et al. |
| 6,147,755 A | | 11/2000 | Heflinger et al. |
| 6,157,448 A | | 12/2000 | Kowa et al. |
| 6,166,807 A | | 12/2000 | Kawamura et al. |

OTHER PUBLICATIONS

Majewski, AJ, 2001, Effects of Ultraviolet Radiation on Optically Active Macromolecules: A study of Type–I Collagen, Dissertation, Stevens Institute of Technology, Hoboken, NJ.

* cited by examiner

Primary Examiner—Samuel A. Turner
Assistant Examiner—Michael A. Lyons
(74) Attorney, Agent, or Firm—Pennie & Edmonds LLP

(57) ABSTRACT

The change in the circular birefringence of a sample is measured by passing a light beam comprised of a left circularly polarized (LCP) wave and a right circularly polarized (RCP) wave through a sample and measuring the change in the phase difference between the RCP and LCP waves.

27 Claims, 6 Drawing Sheets

APPARATUS AND METHOD FOR MEASURING OPTICAL ACTIVITY

FIELD OF THE INVENTION

The present invention relates to the field of measuring the optical properties of materials, in particular the determination of the optical rotatory dispersion, or circular birefringence of a sample.

BACKGROUND OF THE INVENTION

Many biopolymers and macromolecules posses chirality and exhibit optical activity when light is transmitted through the material. Optical activity is defined as the property in which a material absorbs incident radiation and/or changes its polarization state. A material that changes the polarization state of the incident radiation exhibits circular birefringence. A material that absorbs incident radiation depending on the polarization state of the incident radiation exhibits circular dichroism. The optical activity of a substance may be modeled by assigning distinct indices of refraction for left circularly polarized ("LCP") light, $\eta_l$, and for right circularly polarized ("RCP") light, $\eta_r$, where $\eta_l$ and $\eta_r$ are both complex. The difference between the real part of the complex indices of refraction for the LCP and RCP light, $\Delta n = (n_l - n_r) = \text{Re}(\eta_l) - \text{Re}(\eta_r)$, describes the circular birefringence of the material. The difference between the imaginary part of the complex indices of refraction for the LCP and RCP light, $\Delta k = (k_l - k_r) = \text{Im}(\eta_l) - \text{Im}(\eta_r)$, describes the circular dichroism of the material.

Light that is transmitted through a circular birefringent material will exhibit a phase angle rotation, $\alpha$, given by the equation $$\alpha = (\pi d/\lambda_o)(n_l - n_r) \quad (1)$$

where d is the thickness of the sample and $\lambda_o$ is the wavelength of the incident radiation. The difference in the indices of refraction, $(n_l - n_r)$, is referred to as the circular birefringence or rotatory dispersion of the sample In order to measure the phase angle rotation of a sample, traditional systems transmit light of a single known polarization state through the material and measure the polarization state of the transmitted light. The polarization state of the incident light is usually selected by passing the incident light through a linear polarizer ("generating polarizer"). The rotation of the linear polarized light about the optical axis defined by the light beam is measured by passing the light beam exiting the sample through a second linear polarizer ("measurement polarizer") and measuring the transmitted light intensity exiting the measurement polarizer. The measurement polarizer is rotated about the optical axis until the transmitted light intensity is a maximum. The angle of the measurement polarizer with respect to the generating polarizer at maximum transmitted light intensity represents the phase angle rotation of the sample.

The advantage of the traditional systems is that the measurement of the rotation of the measurement polarizer to the generating polarizer is a direct measurement of the circular birefringence of the sample. The disadvantage of the traditional systems is that the resolution and accuracy of the rotation measurement is limited by the polarizers and the mechanical limitations of the polarizer mounting stages. The polarizers are susceptible to thermal fluctuations of the environment that require the user to place the system in a controlled environment and reduce the measurement time as much as possible. This usually requires placing the sample in an enclosed chamber with a closely monitored environment. Placing the sample in a chamber further restricts the type of operations or measurements that can be performed on the sample. As a result of these restrictions, phase measurement systems in current use have resolutions between 1.0–0.1°.

Instead of passing light of a single polarized state through the sample, U.S. Pat. No. 5,896,198 issued on Apr. 20, 1999 to Chou et al. uses an optical heterodyne beam consisting of two linearly polarized waves wherein the polarization planes of the two beam are orthogonal to each other. The beams exiting the sample are passed through an analyzing polarizer. The intensity of the beam is measured by a photodetector and if the rotation of the beam is small, the measured intensity will be proportional to the rotation of the beam. The analyzing polarizer is rotated in a calibration setup that maximizes the transmitted intensity of the beam but is not used to measure the rotation of the beam. The orientation of the polarizer, however, is still important. The rotation of the beam will be proportional to the circular birefringence of the sample only if the two linearly polarized waves remain orthogonal after passing through the sample. In addition, since the rotation is proportional to the transmitted intensity of the beam, small rotations will produce lower intensities such that noise in the detection system or extraneous light sources will limit the minimum resolution of the system.

Therefore, there remains a need for a measuring device that provides for real-time, or instantaneous, measurement of the sample to resolutions of <0.1° while allowing easy access to the sample during the measuring process.

SUMMARY OF THE INVENTION

A light beam comprised of RCP and LCP waves of different frequencies is presented by a beat frequency and a beam phase. The beam phase contains information on the difference between the RCP phase and LCP phase. As the light beam passes through an optically active material, the RCP phase and/or the LCP phase will change. The change in either or both of the RCP phase or LCP phase is contained in the beam phase. Two measurements are made, one with a blank sample and one with the sample. The blank and sample measurements remove any path length or environmental effects from the beam phase. In order to remove any temporal drift effects, each measurement is adjusted by a reference measurement taken at the same time as the blank and sample measurements.

One aspect of the present invention is directed to an apparatus for measuring the circular birefringence of a sample comprising: a light beam generator generating a light beam having a right circularly polarized (RCP) wave characterized by a first frequency and a left circularly polarized (LCP) wave characterized by a second frequency; a beam splitter positioned to receive the light beam from the beam generator and produce a measurement beam and a reference beam; a reference polarizer positioned to receive the reference beam and produce a reference heterodyne wave, the reference heterodyne wave characterized by a reference phase, the reference phase representing the difference between the RCP wave and the LCP wave of the reference beam; a reference detector positioned to receive the reference heterodyne wave and generate a reference signal; a measurement polarizer positioned to receive the measurement beam exiting the sample and produce a measurement heterodyne wave, the measurement heterodyne wave characterized by a measurement phase, the measurement phase representing the difference between the RCP wave and the LCP wave of the measurement beam; a sample detector positioned to receive the measurement heterodyne wave and generate a measurement signal; a gain/phase meter connected to the reference detector and sample detector and generating an output signal characterized by a phase difference equal to the difference between the measurement phase and the reference phase; and a processor connected to the gain/phase meter, the processor calculating the circular birefringence of the sample based, in part, on the output signal of the gain/phase meter.

Another aspect of the present invention is directed to a method for determining the circular birefringence of a sample comprising the steps of: generating a coherent light beam having a left circularly polarized (LCP) wave and a right circularly polarized (RCP) wave, the light beam characterized by a phase; splitting the light beam into a measurement beam and a reference beam; passing the measurement beam through a blank sample; measuring a first phase difference between the measurement beam and reference beam; replacing the blank with the sample and passing the measurement beam through the sample; measuring a second phase difference between the measurement beam and reference beam; and determining the circular birefringence of the sample base, in part, on the first and second phase difference.

BRIEF DESCRIPTION OF THE FIGURES

The present invention may be understood more fully by reference to the following detailed description of the preferred embodiment of the present invention, illustrative examples of specific embodiments of the invention and the appended figures, in which like references refer to like parts throughout, and in which.

DETAILED DESCRIPTION OF THE PREFERRED EMBODIMENT

Figure 1:
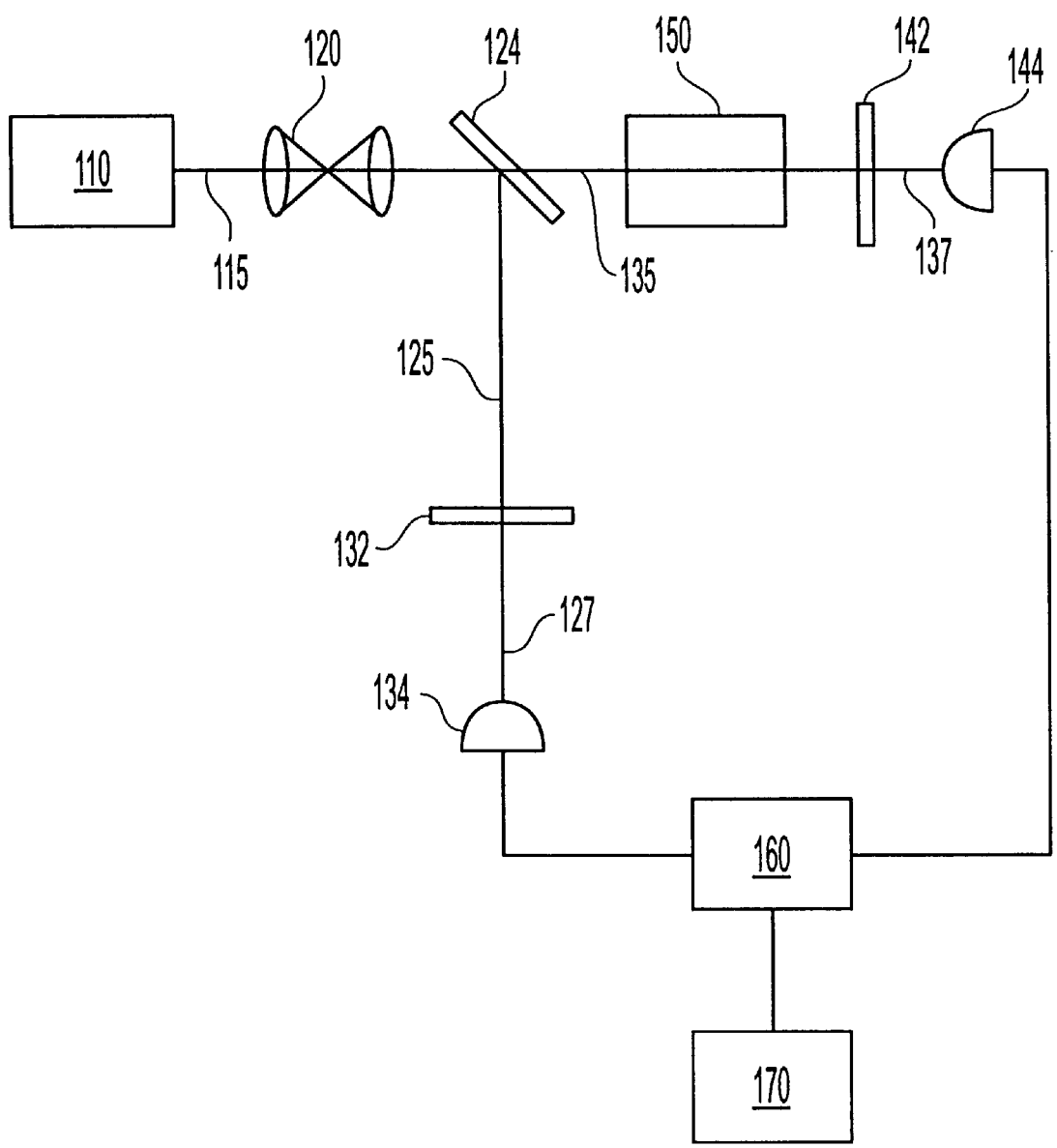
FIG. 1 shows a block diagram of an embodiment of the present invention.

FIG. 1 shows a block diagram of an embodiment of the present invention. Light beam generator 110 emits a coherent light beam 115 comprised of a right-hand circularly polarized ("RCP") wave and a left-hand circularly polarized ("LCP") wave. In a preferred embodiment, the light beam generator 110 is a Zeeman laser tuned to emit the two waves at a frequency difference of 1.73 MHz and a center frequency of about 500 THz. The beam 115 passes through a spatial filter 120 to remove spatial noise and to reduce the beam diameter from an initial diameter of 6 mm to a beam diameter of about 1.5 mm. A beam splitter 124 splits the beam 115 into a reference beam 125 and a measurement beam 135. The beam splitter 124 reflects about 10% of the beam 115 to create the reference beam 125 while the remaining portion of the beam 115 is transmitted through the beam splitter 124 to create the measurement beam 135.

The reference beam 125 contains the phase difference between the RCP and LCP waves emitted by the laser and monitors any phase drift between the RCP and LCP waves caused by the laser. The reference beam 125 is passed through a reference polarizer 132. The reference polarizer 132 causes the LCP and RCP components of the reference beam 125 to interfere in accordance with the Fresnel-Arago laws. The resultant beam 127 will have a heterodyned waveform that is modulated at the beat frequency and characterized by a reference phase, $\phi_{ref}$, that represents the phase difference between the RCP and LCP waves. Since both the RCP and LCP waves have traveled the same path, $\phi_{ref}$ accounts for the arbitrary phase of the RCP and LCP waves generated by the light beam laser 110. A reference detector 134 measures the intensity of the beam 127.

The measurement beam 135 is passed through a sample 150. If the sample is optically active, at least one of the circularly polarized components of the measurement beam 135 will be affected by the sample and the phase difference between the RCP and LCP waves will change. After passing through the sample, the measurement beam 135 passes through a measurement polarizer 142 which causes the LCP and RCP components of the measurement beam 135 to interfere in accordance with the Fresnel-Arago laws. The measurement polarizer 142 and reference polarizer 132 may be any linear polarizer known to one of skill in the optics art. Unlike the polarizers used in traditional systems, however, the measurement polarizer 142 and the reference polarizer 132 are not rotated because they are used only to combine the LCP and RCP waves. Since the only function of the measurement polarizer 142 and reference polarizer 132 is to combine the LCP and RCP waves, the orientation of the polarizers 142, 132 is not critical so the polarizers 142, 132 do not require precision mechanical rotation stages. The beam 137 exiting the measurement polarizer 142 will have a heterodyned waveform that is modulated at the beat frequency and characterized by a measurement phase, $\phi_m$, that represents the phase difference between the RCP and LCP waves. Since both the LCP and RCP components of the measurement beam 135 travel the same path, $\Phi_m$ accounts for the arbitrary phase state of the waves generated by the light beam generator 110 and by the optical activity of the sample. A sample detector 144 measures the intensity of the beam exiting the measurement polarizer 142.

The signals generated by the reference detector 134 and sample detector 144 are combined at a gain/phase meter 160. An illustrative gain/phase meter is the HP3575SA gain/phase meter from Hewlett-Packard Company of Palo Alto, Calif. The gain/phase meter 160 determines the phase difference, $\Delta\Phi=\phi_m-\phi_{ref}$, between the phase of the measurement beam and the phase of the reference beam. The phase difference is given by the following equation $$\Delta\Phi = \left(\frac{2\pi}{c}\right)(f_b x_\Delta + f_c d\Delta n) \qquad (2)$$

where c is the speed of light in vacuum, $f_b$ is the beat frequency of the beam 115, $f_c$ is the center frequency of the beam 115, d is the sample thickness, and $x_\Delta = x_m - x_{ref}$ where $x_m$ is the distance from the laser 110 to the sample detector 144 and $x_{ref}$ is the distance from the laser 110 to the reference detector 134.

The output of the gain/phase meter 160 is transmitted to a processor 170, such as a PC or workstation, for further processing, storage, and/or display. The processor 170 is capable of executing a control program that determines the circular birefringence of the sample, based, in part, on the display out put of the gain/phase meter 160 and equations 1–2.

Figure 2:
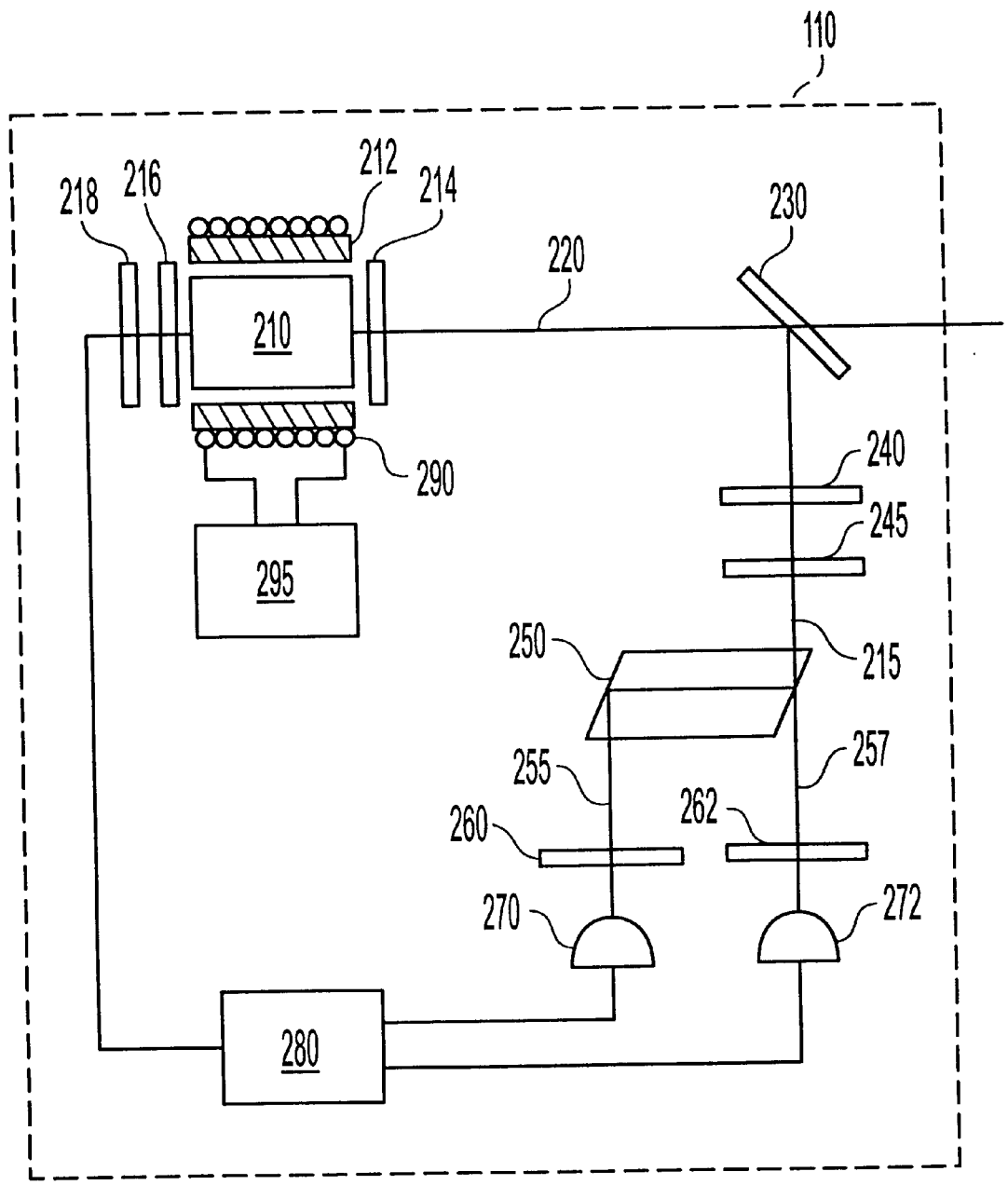
FIG. 2 shows a block diagram of the Zeeman laser system of the embodiment shown in FIG. 1.

FIG. 2 shows a block diagram of the laser beam generator used to generate the two collinear, orthogonal, linearly polarized electromagnetic waves. A laser cavity 210 is filled with a laser material, preferably He—Ne. The upper and lower laser states of the laser material are selected such that the transition from the upper to lower laser state produces both LCP and RCP electromagnetic radiation. A permanent magnet 212 circumferentially surrounding the laser cavity 210 creates an axial magnetic field within the laser cavity 210 and is aligned with the longitudinal axis of the laser cavity 210. The magnetic field splits the degenerate states of the neon atoms thereby creating the laser states necessary for generating the LCP and RCP radiation. The strength of the magnetic field determines the frequency difference between the LCP and RCP waves, also referred to as the beat frequency of the LCP and RCP waves.

Mirrors 214, 216 cover the ends of the laser cavity 210. Rear mirror 216 is highly reflective but the front mirror 214 is partially reflective. The rear mirror 216 may be axially displaced by a PZT transducer 218 thereby varying the length between the mirrors 214, 216. The length between the mirrors 214, 216 affects the frequency of the radiation emitted by the laser so that controlling the length between the mirrors 214, 216 via the PZT transducer 218 allows one to "tune" the laser to a desired center frequency.

The permanent magnet 212 is preferably selected to provide a field strength such that the beat frequency of the LCP and RCP waves is 1.73 MHz. The circularly polarized waves exit the laser cavity 210 along the beam axis 220.

A feedback beam-splitter 230 reflects a small portion of the beam 220 through a quarter-wave plate 240 followed by a half-wave plate 245. The quarter-wave plate 240 converts the LCP and RCP waves to two collinear, orthogonal, linearly polarized electromagnetic waves. The half-wave plate 245 adjusts the relative phase difference between the two linearly polarized waves to correct for imperfections in the quarter-wave plate 240 so that the two linearly polarized waves are orthogonal to each other. The feedback beam 225 exiting the half-wave plate 245 is passed through a polarizing beam-splitter 250 that splits the feedback beam 225 into its two linearly polarized components 255, 257. Each of the component beams 255, 257 is passed through a polarizer 260, 262. Sample detectors 270, 272 measure the intensity of each component beam 255, 257 and a signal representing the intensity of each component beam 255, 257 is transmitted to a center frequency controller 280. The center frequency controller 280 varies the voltage applied to the PZT transducer 218 to keep the intensities of the component beams 255, 257 equal to each other.

The permanent magnet 212 generates a fairly constant magnetic field sufficient to keep the beat frequency, the frequency difference between the LCP and RCP waves, at around 1.73 MHz. Stray magnetic fields or thermal fluctuations, however, cause the beat frequency to vary by as much as 10 kHz. In order to reduce the variations in the beat frequency, a secondary axial magnetic field is created in the laser cavity 210. The secondary magnetic field is created by a stabilizer coil 290 wrapped around the permanent magnet 212. The stabilizer coil 290 is energized by beat controller 295. The beat controller 295 compares an internally generated frequency, preferably 1.73 MHz, to the beat frequency of the beam 220 and adjusts the current to the stabilizer coil 290 until the beat frequency of the beam 220 matches the internally generated frequency. The addition of the stabilizer coil 290 and beat controller 295 reduced the variation in the beat frequency, in one embodiment of the present invention, from 10 kHz to less than 100 Hz. In a preferred embodiment, the variation in the beat frequency is about 70 Hz.

Figure 3:
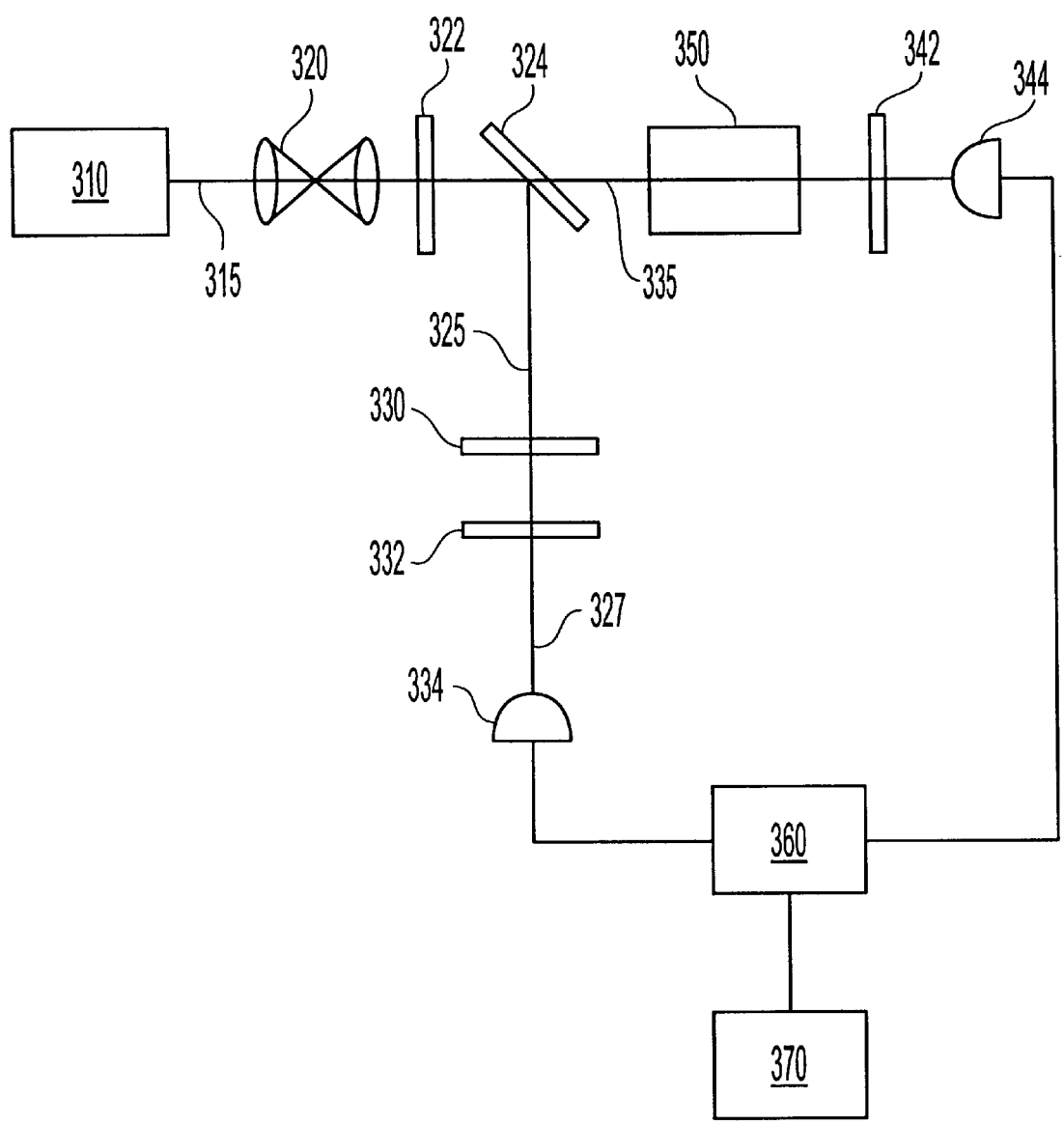
FIG. 3 shows a block diagram of another embodiment of the present invention.

FIG. 3 shows a block diagram of another embodiment of the present invention wherein like elements bear the same number as in FIG. 1 but incremented by two hundred (200). A light beam generator 310 emits a beam 315 comprised of two collinear, orthogonally, linearly polarized electromagnetic waves. In a preferred embodiment, the light beam generator 310 is a Zeeman laser available as the Agilent 5501B Laser Head from Agilent Technologies of Palo Alto, Calif. The two waves emitted by the Zeeman laser have a frequency difference of 1.73 MHz. The beam 315 passes through a spatial filter 320 to remove spatial noise and to reduce the beam diameter from an initial diameter of 6 mm to a beam diameter of about 1.5 mm. After exiting the spatial filter 320, the beam 315 passes through a quarter-wave plate 322. The quarter-wave plate 322 converts the two orthogonal linearly polarized waves of the beam 315 into right circularly polarized ("RCP") and left circularly polarized ("LCP") waves. A beam splitter 324 splits the beam 315 into a reference beam 325 and a measurement beam 335. The beam splitter 324 reflects about 10% of the beam 315 to create the reference beam 325 while the remaining portion of the beam 315 is transmitted through the beam splitter 324 to create the measurement beam 335.

The reference beam 325 is passed through a half-wave plate 330. The reference beam 325 contains the phase difference between the RCP and LCP waves emitted by the laser and monitors any phase drift between the RCP and LCP waves caused by the laser. The half-wave plate 330 may be rotated to adjust the relative phase between the two circularly polarized waves of the reference beam. The adjustment is made to position the relative phase away from the $\pi$ and $2\pi$ singularities. After exiting the half-wave plate 330, the reference beam 325 is passed through a reference polarizer 332. The reference polarizer 332 causes the LCP and RCP components of the reference beam 325 to interfere in accordance with the Fresnel-Arago laws. The resultant beam 327 enters a reference detector 334 that measures the intensity of the beam 327.

The measurement beam 335 is passed through a sample 350. If the sample is optically active, at least one of the circularly polarized components of the measurement beam 335 will be affected by the sample and the phase difference between the RCP and LCP waves will change. After passing through the sample, the measurement beam 335 passes through a measurement polarizer 342 which causes the LCP and RCP components of the measurement beam 335 to interfere in accordance with the Fresnel-Arago laws. A sample detector 344 measures the intensity of the beam exiting the measurement polarizer 342.

The signals generated by the reference detector 334 and sample detector 344 are combined at a gain/phase meter 360 that measures the phase difference between the reference beam 325 and the measurement beam 335. An illustrative gain/phase meter is the HP3575SA gain/phase meter from Hewlett-Packard Company of Palo Alto, Calif. The output of the gain/phase meter 360 is transmitted to a processor 370 for further processing, storage, and/or display.

The gain/phase meter 360 determines the phase difference, $\Delta\Phi=\phi_m-\Phi_{ref}$, between the phase of the measurement beam and the phase of the reference beam. Equation 2, however, cannot be used to determine the circular birefringence of the sample because of the bias added to $\phi_{ref}$ by the half-wave plate 330. The change in the phase difference is given by $$\delta(\Delta\Phi) = \frac{2\pi d \delta(\Delta n)}{\lambda_o} \quad (3)$$

where $\lambda_o$ is the wavelength corresponding to the center frequency of the Zeeman laser. Once the bias has been added to $\phi_{ref}$ by the half-wave plate 330, any change in the phase difference determined by the gain/phase meter can only be due to the change in $\Delta n$ of the sample. The change in $\Delta n$ may be due to a change in the sample from a blank sample to a material sample. The $\Delta n$ in such a case would correspond to the circular birefringence of the material. In another application of the present invention, the change in the circular birefringence of a sample may be monitored by continuously measuring $\Delta\Phi$ as the condition of the sample is changed. For example, the circular birefringence of a material may be determined by measuring $\Delta\Phi$ as a function of temperature as the material is heated.

Figure 4:
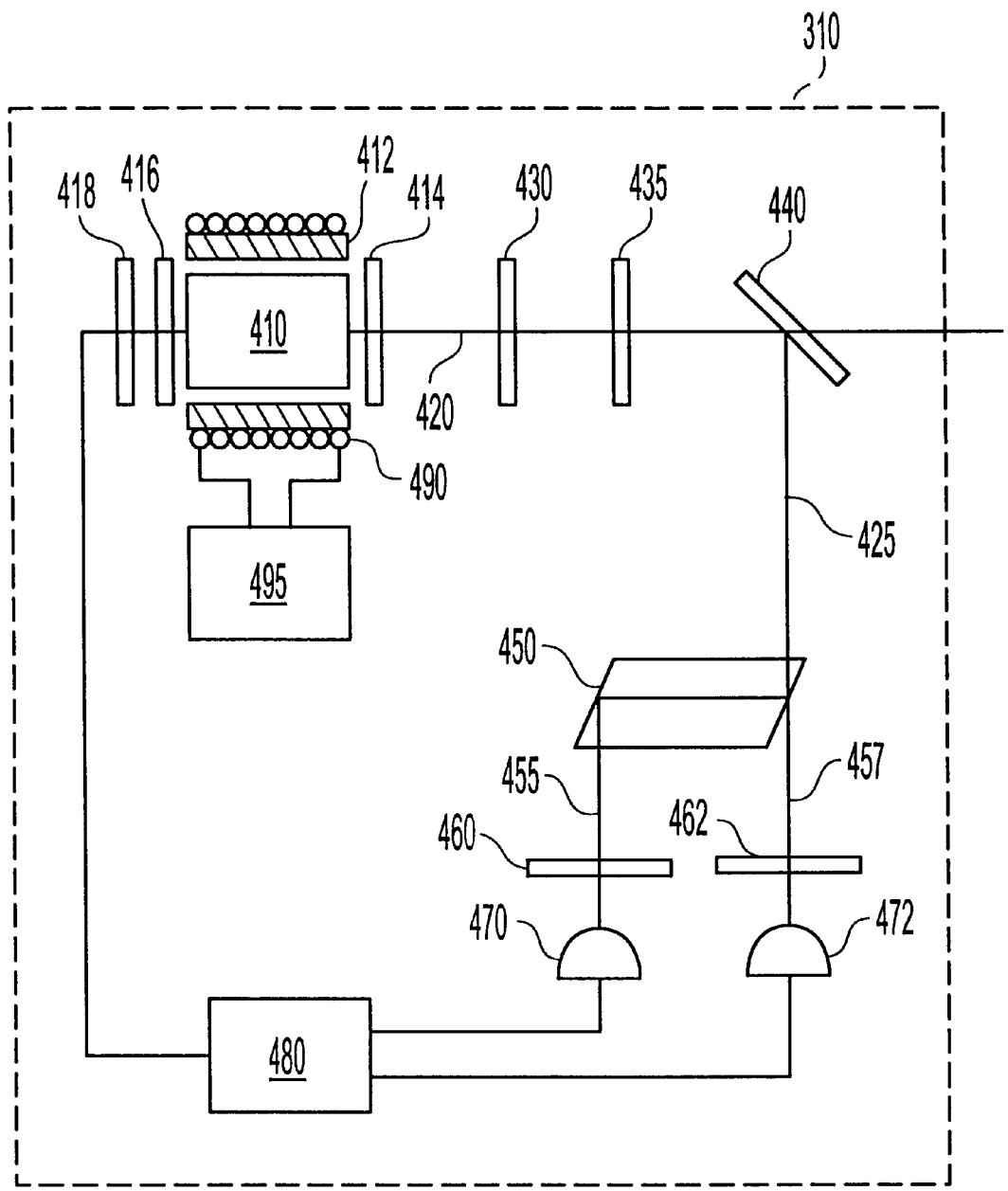
FIG. 4 shows a block diagram of the Zeeman laser system of the embodiment shown in FIG. 3.

FIG. 4 shows a block diagram of the laser system used to generate the two collinear, orthogonal, linearly polarized electromagnetic waves wherein like elements bear the same number as in FIG. 2 but incremented by two hundred (200). A laser cavity 410 is filled with a laser material, preferably He—Ne. The upper and lower laser states of the laser material are selected such that the transition from the upper to lower laser state produces both LCP and RCP electromagnetic radiation. A permanent magnet 412 circumferentially surrounding the laser cavity 410 creates an axial magnetic field within the laser cavity 410 and is aligned with the longitudinal axis of the laser cavity 410. The magnetic field splits the degenerate states of the neon atoms thereby creating the laser states necessary for generating the LCP and RCP radiation. The strength of the magnetic field determines the frequency difference between the LCP and RCP waves.

Mirrors 414, 416 cover the ends of the laser cavity 410. Rear mirror 416 is highly reflective but the front mirror 414 is partially reflective. The rear mirror 416 may be axially displaced by a PZT transducer 418 thereby varying the length between the mirrors 414, 416. The length between the mirrors 414, 416 affects the frequency of the radiation emitted by the laser so that controlling the length between the mirrors 414, 416 via the PZT transducer 418 allows one to "tune" the laser to a desired frequency.

The permanent magnet 412 is preferably selected to provide a field strength such that the beat frequency of the LCP and RCP waves is 1.73 MHz. The circularly polarized waves exit the laser cavity 410 along the beam axis 420 and pass through a quarter-wave plate 430 and a half-wave plate 435. The quarter-wave plate 430 converts the LCP and RCP waves to two collinear, orthogonal, linearly polarized electromagnetic waves. The half-wave plate 435 adjusts the relative phase difference between the two linearly polarized waves to correct for imperfections in the quarter-wave plate 430 so that the two linearly polarized waves are orthogonal to each other.

A beam-splitter 440 reflects a small portion of the beam 420 into a polarizing beam-splitter 450 that splits the feedback beam 425 into its two linearly polarized components 455, 457. Each of the component beams 455, 457 is passed through a polarizer 460, 462. Sample detectors 470, 472 measure the intensity of each component beam 455, 457 and a signal representing the intensity of each component beam 455, 457 is transmitted to a center frequency controller 480. The center frequency controller 480 varies the voltage applied to the PZT transducer 418 to keep the intensities of the component beams equal to each other.

The permanent magnet 412 generates a fairly constant magnetic field sufficient to keep the beat frequency, the frequency difference between the LCP and RCP waves, at around 1.73 MHz. Stray magnetic fields or thermal fluctuations, however, cause the beat frequency to vary by as much as 10 kHz. In order to reduce the variations in the beat frequency, a secondary axial magnetic field is created in the laser cavity 410. The secondary magnetic field is created by a stabilizer coil 490 wrapped around the permanent magnet 412. The stabilizer coil 490 is energized by beat controller 495. The beat controller 495 compares an internally generated frequency, preferably 1.73 MHz, to the beat frequency of the beam 420 and adjusts the current to the stabilizer coil 490 until the beat frequency of the beam 420 matches the internally generated frequency. The addition of the stabilizer coil 490 and beat controller 495 reduced the variation in the beat frequency, in one embodiment of the present invention, from 10 kHz to 70 Hz.

Processor 170, 370 includes a processing unit, a memory unit, an input device, and an output device. The processing unit is capable of executing a program stored in the memory unit, retrieving data stored in the memory unit, saving data to the memory unit, accepting data from the input unit, and sending data to the output device. The processor 170, 370 may be a PC or any equivalent device known to one of skill in the art. In a preferred embodiment, the processor executes a program that determines the change in the circular birefringence of a sample during a measurement by first storing the measured phase differences from the gain/phase meter 160, 360 in the memory unit. The change in the circular birefringence of the sample is then calculated using $$\delta(\Delta n) = \frac{2\pi d \delta(\Delta\Phi)}{\lambda_o} \quad (4)$$

where $\delta(\Delta n)$ is the change in circular birefringence of the sample between a first measurement and a second measurement, d is the sample thickness, $\lambda_o$ is the center frequency of the RCP and LCP waves, and $\delta(\Delta\Phi)$ is the change in the phase differences between the first measurement and the second measurement. The constant, $2\pi$, along with d and $\lambda_o$, are stored in the memory unit. If a blank sample (a sample not containing the optically active material of interest) is used in the first measurement and a sample containing the optically active material of interest is used in the second measurement, the change in circular birefringence will represent the circular birefringence of the optically active material. As will be clear to one of skill in the art, the first and second measurements of the phase difference is not limited to a single measurement of the phase difference, and a plurality of phase difference measurements may be made by the gain/phase meter 160, 360 and stored in the memory unit.

The processor 170, 370 may also convert measured circular birefringence into the specific rotation, $[\alpha]_\lambda$, given by $$[\alpha]_\lambda = \frac{10\pi\Delta n}{\lambda_o \rho} \quad (5)$$

where $\rho$ is the concentration of the optically active material in grams per milliliter and $\lambda_o$ is the center wavelength in meters.

The long term stability of the present invention and the ability to make measurements on a sample as it is being irradiated is now summarized with respect to the effect of ultraviolet irradiation on the denaturation of collagen. The details and experimental results are presented in Majewski, Alexander *Effects of Ultraviolet Radiation on Optically Active Molecules: A Study of Type I Collagen* Ph.D. Thesis, Stevens Institute of Technology, Hoboken, N.J. (May 4, 2001) and is herewith incorporated by reference in its entirety.

Collagen is the most abundant protein in the human body with approximately 20 different identifiable types. The collagen molecule has a triple-helix structure consisting of three polypeptide chains wrapped around each other. The triple-helix has a structural repeating distance of approximately 8.6 nm and an overall length of about 300 nm. The main stabilizing forces in the collagen triple-helix are the extensive hydrogen bonding within the molecule. The molecule may be de-stabilized by changing the environment of the molecule such as temperature or pH. Heating collagen above its denaturation temperature, $T_d$, induces denaturation and causes the molecule to unravel. The change from a triple-helix structure, which is optically active, to a denatured structure, which is not optically active, is easily measured by the present invention.

The collagen used in this example consisted of pepsin treated, type-I bovine collagen in a 0.012 N HCl solution. The pepsin treatment removed the telopeptides at the ends of the triple-helix structure and ensured that samples consisted of non cross-linked triple helices. The collagen concentration was 3.15 mg/ml. The collagen solutions were contained in 20-mm and 40 mm quartz cuvettes that were annealed to relieve any stress birefringence. Both types of cuvettes had two optically polished faces through which the measurement beam propagated.

Figure 5:
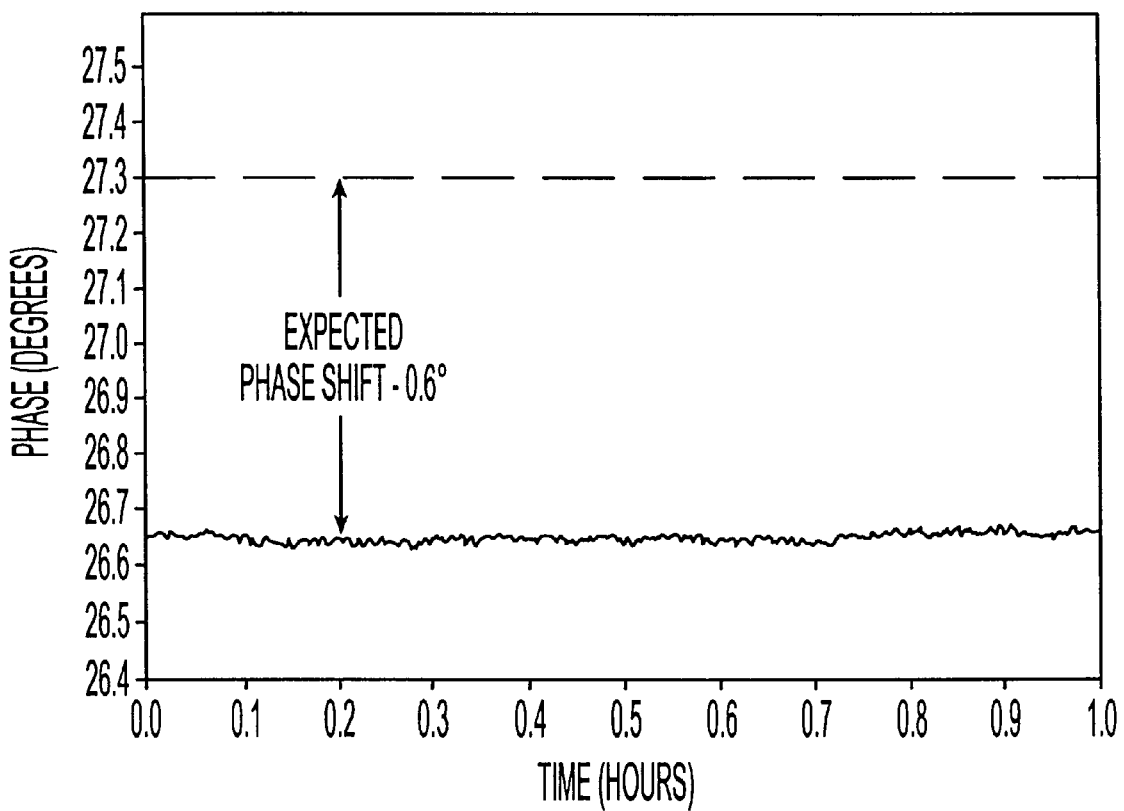
FIG. 5 shows the temporal stability of an embodiment of the present invention.

As a preliminary study, the temporal stability of an embodiment of the present invention was demonstrated by running the device for one hour. FIG. 5 shows the system stability over one hour (the estimated duration of an individual experiment) and shows that the variation of the measured phase is less than 0.02°. FIG. 5 also illustrates the point that, unlike traditional methods that measure the absolute circular birefringence of a sample, the system in FIG. 5 measures the change in the circular birefringence of a sample. The numerical value of the phase at a given time is arbitrary but the difference between two phase values at different times reflects the change in circular birefringence of the sample between the two times. The long term stability of the system enables the experimenter to make the phase measurements at different times because the reference leg accounts for any drift of the beam generator and the co-propagating LCP and RCP waves of the measurement beam account for environmental differences along the measurement path.

Blank samples of 0.012 N HCl solution contained in the cuvettes where placed in the measurement beam path of the system and were heated and/or irradiated. Ultraviolet light from a 100 W high-pressure mercury arc lamp was used to irradiate the sample. These experiments verified that the cuvettes filled with the HCl solution did not produce a permanent phase shift due to stress birefringence.

Figure 6:
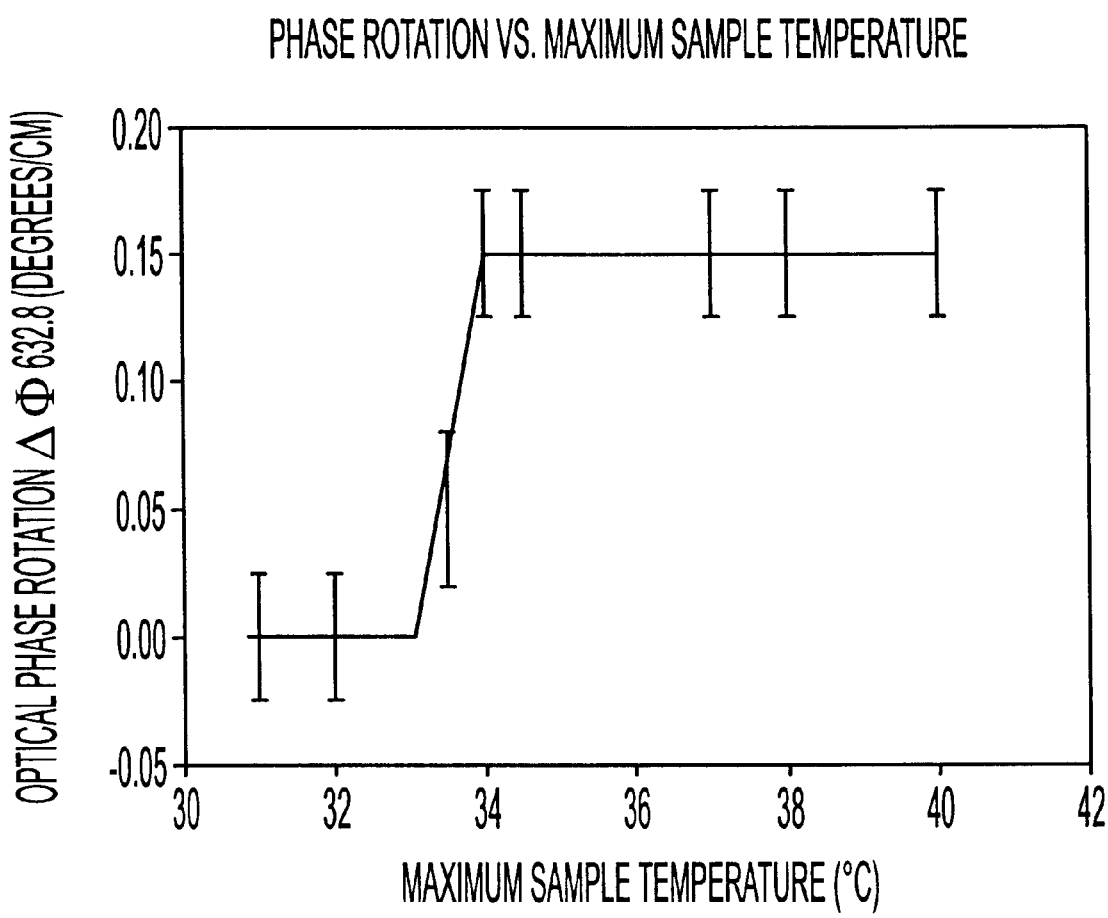
FIG. 6 shows the optical phase rotation of pepsin treated type-I bovine collagen in a 0.012 N HCl solution as a function of temperature.

FIG. 6 shows the optical phase rotation of pepsin treated type-I bovine collagen in a 0.012 N HCl solution as a function of temperature during broadband ultraviolet irradiation. The collagen solution was placed in a 4 cm quartz cuvette and held at temperature while being irradiated from a mercury arc lamp. FIG. 5 shows a change in the optical phase rotation between a temperature of 33° C. and 34° C. The 0.6° rotation measured by the present invention corresponds to the transition of the collagen from its native helical state that is optically active to its denatured coiled state that does not exhibit optical activity.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An apparatus for measuring the circular birefringence of a sample comprising:

(a) a reference polarizer positioned to receive a reference beam having a right circularly polarized (RCP) wave characterized by a first frequency and a left circularly polarized (LCP) wave characterized by a second frequency, the reference polarizer producing a reference heterodyne wave, the reference heterodyne wave characterized by a reference phase, the reference phase representing the difference between the RCP wave and the LCP wave of the reference beam;

(b) a reference detector positioned to receive the reference heterodyne wave and generate a reference signal;

(c) a measurement polarizer positioned to receive a measurement beam exiting the sample, the measurement beam having a RCP wave characterized by the first frequency and a LCP wave characterized by the second frequency, the measurement polarizer producing a measurement heterodyne wave, the measurement heterodyne wave characterized by a measurement phase, the measurement phase representing the difference between the RCP wave and the LCP wave of the measurement beam;

(d) a sample detector positioned to receive the measurement heterodyne wave and generate a measurement signal;

(e) a gain/phase meter connected to the reference detector and sample detector and generating an output signal characterized by a phase difference equal to the difference between the measurement phase and the reference phase; and (f) a control program capable of execution on a processor, the control program calculating the circular birefringence of the sample based, in part, on the output signal of the gain/phase meter.

2. The apparatus of claim 1 wherein the reference beam and measurement beam are generated by a Zeeman laser characterized by a center frequency and a beat frequency.

3. The apparatus of claim 2 wherein the Zeeman laser includes a permanent magnet and a stabilizer coil, the stabilizer coil energized to maintain a beat frequency having a variation less than 100 Hz.

4. The apparatus of claim 3 wherein the Zeeman laser further includes a quarter-wave plate, the quarter-wave plate converting a portion of the LCP and RCP waves into a first linearly polarized (1 LP) wave and a second linearly polarized (2LP) wave, the 1LP wave orthogonal to the 2LP wave.

5. The apparatus of claim 1 wherein the measurement polarizer is fixed with respect to rotations about an axis defined by the measurement beam.

6. The apparatus of claim 2 wherein the beat frequency is less than 200 MHz.

7. The apparatus of claim 6 wherein the beat frequency is less than 10 MHz.

8. The apparatus of claim 7 wherein the beat frequency is between 0.5 MHz–4 MHz.

9. The apparatus of claim 8 wherein the beat frequency is between 1.5 MHz–2.0 MHz.

10. The apparatus of claim 1 further comprising:
   (i) a light beam generator generating a light beam having a first linearly polarized (1LP) wave characterized by a first frequency and a first polarization plane and a second linearly polarized (2LP) wave characterized by a second frequency and a second polarization plane, wherein the first polarization plane is orthogonal to the second polarization plane;
   (ii) a quarter-wave plate positioned to receive the light beam and convert the first and second linearly polarized waves to a right circularly polarized (RCP) wave and a left circularly polarized (LCP) wave; and
   (iii) a beam splitter positioned to receive the light beam from the quarter-wave plate and produce a measurement beam and a reference beam.

11. The apparatus of claim 10 wherein the light beam generator is a Zeeman laser characterized by a center frequency and a beat frequency.

12. The apparatus of claim 11 wherein the Zeeman laser includes a permanent magnet and a stabilizer coil, the stabilizer coil energized to maintain a beat frequency having a variation less than 100 Hz.

13. The apparatus of claim 10 wherein the measurement polarizer is fixed with respect to rotations about an axis defined by the measurement beam.

14. The apparatus of claim 11 wherein the beat frequency is less than 200 MHz.

15. The apparatus of claim 14 wherein the beat frequency is less than 10 MHz.

16. The apparatus of claim 15 wherein the beat frequency is between 0.5 MHz–4 MHz.

17. The apparatus of claim 16 wherein the beat frequency is between 1.5 MHz–2.0 MHz.

18. A method for determining the circular birefringence of a sample comprising the steps of:
   (a) generating a coherent light beam having a left circularly polarized (LCP) wave and a right circularly polarized (RCP) wave, the light beam characterized by a phase;
   (b) splitting the light beam into a measurement beam and a reference beam;
   (c) passing the measurement beam through a blank sample;
   (d) measuring a first phase difference between the measurement beam and reference beam;
   (e) replacing the blank with the sample and passing the measurement beam through the sample;
   (f) measuring a second phase difference between the measurement beam and reference beam; and
   (g) determining the circular birefringence of the sample based, in part, on the first and second phase difference.

19. The method of claim 18 wherein the coherent light beam is generated by a Zeeman laser.

20. The method of claim 19 wherein the Zeeman laser includes a stabilizer coil, the stabilizer coil energized to maintain a beat frequency having a variation of less than 100 Hz.

21. The method of claim 18 wherein the steps (b) and (f) of measuring further include the steps of:
   (i) passing the measurement beam and reference beam through a polarizer;
   (ii) detecting a measurement beam intensity and a reference beam intensity; and
   (iii) measuring the phase difference between the measurement beam and reference beam based, in part, on the measurement beam intensity and reference beam intensity.

22. A method for determining the circular birefringence of a sample comprising the steps of:
   (a) generating a coherent light beam having a left circularly polarized (LCP) wave and a right circularly polarized (RCP) wave, the light beam characterized by a phase;
   (b) splitting the light beam into a measurement beam and a reference beam;
   (c) passing the measurement beam through a sample;
   (d) measuring a phase difference between the measurement beam and reference beam;
   (e) repeating steps (c) and (d) at least once thereby measuring a plurality of phase differences; and
   (f) determining the circular birefringence of the sample based, in part, on the plurality of phase differences.

23. The method of claim 22 wherein the step of measuring further includes the steps of:
   (i) passing the measurement beam and reference beam through a polarizer;
   (ii) detecting a measurement beam intensity and a reference beam intensity; and
   (iii) measuring the phase difference between the measurement beam and reference beam based, in part, on the measurement beam intensity and reference beam intensity.

24. The method of claim 22 wherein the LCP wave is characterized by a first frequency and the RCP wave is characterized by a second frequency wherein the first frequency is not equal to the second frequency.

25. A method for measuring the change of the circular birefringence of a sample comprising the steps of:
   (a) propagating a beam through a sample, the beam having a first wave characterized by a first polarization state and a second wave characterized by a second polarization state that is orthogonal to the first polarization state, the beam further characterized by a phase difference between the first and second wave; and
   (b) measuring the change of the phase difference of the beam.

26. An apparatus for measuring the circular birefringence of a sample comprising:
   (a) a light beam generator generating a light beam having a right circularly polarized (RCP) wave characterized by a first frequency and a left circularly polarized (LCP) wave characterized by a second frequency;
   (b) a beam splitter positioned to receive the light beam from the beam generator and produce a measurement beam and a reference beam;
   (c) a reference polarizer positioned to receive the reference beam and produce a reference heterodyne wave, the reference heterodyne wave characterized by a reference phase, the reference phase representing the difference between the RCP wave and the LCP wave of the reference beam;

(d) a reference detector positioned to receive the reference heterodyne wave and generate a reference signal;

(e) a measurement polarizer positioned to receive the measurement beam exiting the sample and produce a measurement heterodyne wave, the measurement heterodyne wave characterized by a measurement phase, the measurement phase representing the difference between the RCP wave and the LCP wave of the measurement beam;

(f) a sample detector positioned to receive the measurement heterodyne wave and generate a measurement signal;

(g) a gain/phase meter connected to the reference detector and sample detector and generating an output signal characterized by a phase difference equal to the difference between the measurement phase and the reference phase; and (h) a processor connected to the gain/phase meter, the processor calculating the circular birefringence of the sample based, in part, on the output signal of the gain/phase meter.

27. An apparatus for measuring the circular birefringence of a sample comprising:

(a) a light beam generator generating a light beam having a first linearly polarized (1LP) wave characterized by a first frequency and a first polarization plane and a second linearly polarized (2LP) wave characterized by a second frequency and a second polarization plane, wherein the first polarization plane is orthogonal to the second polarization plane;

(b) a quarter-wave plate positioned to receive the light beam and convert the first and second linearly polarized waves to a right circularly polarized (RCP) wave and a left circularly polarized (LCP) wave;

(c) a beam splitter positioned to receive the light beam from the quarter-wave plate and produce a measurement beam and a reference beam;

(d) a reference polarizer positioned to receive the reference beam and produce a reference heterodyne wave, the reference heterodyne wave characterized by a reference phase, the reference phase representing the difference between the RCP wave and the LCP wave of the reference beam;

(e) a reference detector positioned to receive the reference heterodyne wave and generate a reference signal;

(f) a measurement polarizer positioned to receive the measurement beam exiting the sample and produce a measurement heterodyne wave, the measurement heterodyne wave characterized by a measurement phase, the measurement phase representing the difference between the RCP wave and the LCP wave of the measurement beam;

(g) a sample detector positioned to receive the measurement heterodyne wave and generate a measurement signal;

(h) a gain/phase meter connected to the reference detector and sample detector and generating an output signal characterized by a phase difference equal to the difference between the measurement phase and the reference phase; and (i) a processor connected to the gain/phase meter, the processor calculating the circular birefringence of the sample based, in part, on the output signal of the gain/phase meter.

* * * * *